(12) United States Patent
Gerdes

(10) Patent No.: US 8,249,699 B2
(45) Date of Patent: Aug. 21, 2012

(54) METHOD OF AFFECTING BALANCED BRAIN FUNCTION WITH RELATIONAL AMBIENT SOUND

(75) Inventor: Lee Gerdes, Scottsdate, AZ (US)

(73) Assignee: Brain State Technologies, LLC, Scottsdale, AZ (US)

( * ) Notice: Subject to any disclaimer, the term of this patent is extended or adjusted under 35 U.S.C. 154(b) by 482 days.

(21) Appl. No.: 12/483,979

(22) Filed: Jun. 12, 2009

(65) Prior Publication Data

US 2009/0281447 A1 Nov. 12, 2009

Related U.S. Application Data

(63) Continuation-in-part of application No. 11/347,169, filed on Feb. 3, 2006, now abandoned.

(51) Int. Cl.
*A61B 5/04* (2006.01)

(52) U.S. Cl. .................. 600/544; 600/545

(58) Field of Classification Search .................. 600/544, 600/545
See application file for complete search history.

(56) References Cited

U.S. PATENT DOCUMENTS

| | | | | |
|---|---|---|---|---|
| 4,834,701 A * | 5/1989 | Masaki | ................. | 600/28 |
| 4,883,067 A * | 11/1989 | Knispel et al. | ................. | 600/545 |
| 5,474,082 A * | 12/1995 | Junker | ................. | 600/545 |
| 6,480,743 B1 * | 11/2002 | Kirkpatrick et al. | ................. | 607/45 |
| 6,547,746 B1 * | 4/2003 | Marino | ................. | 600/554 |
| 2005/0043646 A1 * | 2/2005 | Viirre et al. | ................. | 600/545 |
| 2009/0247895 A1 * | 10/2009 | Morikawa et al. | ................. | 600/544 |

\* cited by examiner

*Primary Examiner* — Navin Natnithithadha

(74) *Attorney, Agent, or Firm* — Weiss & Moy, P.C.; Veronica-Adele R. Cao

(57) ABSTRACT

A method for affecting balanced brain functioning with relational ambient sound is disclosed. During the process of balancing the brain's activity, an ambient sound is played for the subject to hear. The subject's brain develops a relationship between the process of bringing the brain to a balanced state and the ambient sound. As a result of this relationship, balanced brain functioning may then be affected by exposing the subject to that same ambient sound.

21 Claims, 2 Drawing Sheets

METHOD OF AFFECTING BALANCED BRAIN FUNCTION WITH RELATIONAL AMBIENT SOUND

CROSS-REFERENCE TO RELATED APPLICATION

This is a continuation-in-part of U.S. patent application Ser. No. 11/347,169 filed Feb. 3, 2006 now abandoned in the name of the Applicant, to which priority is claimed.

FIELD OF THE INVENTION

This invention relates generally to neurological functioning and, more particularly, to a method that seeks to automatically balance brainwaves in an individualized manner, consistent with optimized cognitive performance by establishing a relationship between balanced functioning (homeostasis) and an outside stimulus. Cognitive functioning refers to the mental processes by which knowledge is acquired. These mental processes include perception, reasoning, acts of creativity, problem-solving, and possible intuition.

BACKGROUND OF THE INVENTION

The high amount of stress in daily life is caused by increased demands on our time. Persons in the work force are being asked to produce more in a shorter amount of time, family activities are heavily scheduled, and the amount of electronic stimuli to which persons in developed countries are exposed has grown exponentially in the last several decades. The intensity to accomplish more in less time is the basic component for stress in daily life. Stress causes the brain to tighten; oxygen is utilized from the blood more slowly, and brain functioning and processing slows. In general, stress causes reduced efficiency of the brain power required to accomplish cognitive functioning.

There are a great number of activities known to help reduce stress—breathing exercises, regular physical exercise, meditation, yoga, and others. However, these activities are for the purpose of reducing stress after it has already manifested, rather than preventing stress from having such a damaging affect on optimized brain functioning. Stress affects a person as if the individual who has stress is a container and stress is a substance that is poured into it. The stress-reducing activities help "pour out" the stress from the container, or person. These activities are helpful as responses to an over-full container. They are not helpful to reduce the container from getting full in the first place. These activities empty the container rather than prevent it from being filled—they are prescriptive rather than preventative. And, after the person is affected by stress to a significant degree, the person then experiences decreased cognitive functioning, which often then causes even greater stress, with the result that the container gets more stress poured into it. This merry-go-round effect leads the stress spiral to poorer and less efficient cognitive performance. Additionally, those stress reducing methods do not condition the brain so that the brain is aware that the stress response to certain stimuli is unhelpful to its optimized functioning.

Brain activity creates electromagnetic energy—captured and observed as brainwaves with EEG amplifiers and computers—which indicate how the brain is functioning. Brain activity is based on neurons which interact and connect with each other to form groups known as "neuro-nets". These neuro-nets are activated based on stimuli. As a consequence, when a certain stimulus is experienced—like a mouse jumping out from behind a counter—we have a brief moment of fear and jump back. This occurs because neuro-nets were activated that created a pathway for us to jump, for our hearts to race a bit, and possibly for us to utter a noise in response to such stimulus.

Neurofeedback, which exposes a person to sound waves at certain predetermined frequencies, has also been used to deal with brain functioning. For example, one neurofeedback method is based on a Quantitative Electroencephalographic Analysis (QEEG). Using a QEEG, the neurofeedback provider compares the brainwaves of the client to a normative data base of other brainwaves. Following such comparison, irregularities are noted for neurofeedback training. A significant problem with a QEEG, however, is the basic assumption that the database of brainwaves is helpful to establish a normal or healthy brainwave pattern for all individuals. This is not always so.

The present invention provides a method for affecting balanced brain activity that is individualized, in order to more effectively condition the particular subject's brain while it is working to be optimized for cognitive functioning. During the process of balancing the brain's activity (returning the brain to homeostatic conditions), an outside stimulus, such as ambient sound, is played for the subject to hear. The subject's brain develops a relationship between the process of bringing the brain to a balanced state and the outside stimulus. Because the brain remembers this relationship, balanced brain functioning may then later be affected by exposing the subject to the exact same outside stimulus.

SUMMARY OF THE INVENTION

In accordance with an embodiment of the present invention, a method for affecting balanced brain functioning is disclosed. The method comprises the steps of determining a baseline brain activity of a subject as reflected in electromagnetic waves emitted by the brain of the subject, altering brain activity until the brain functions within an optimal frequency range, and establishing a relationship between the step of altering brain activity and an outside stimulus.

In accordance with another embodiment of the present invention, a method for affecting balanced brain functioning with relational sound is disclosed. The method comprises the steps of placing at least two sensors on a scalp of a subject to detect brainwave frequencies in at least one area of the brain, monitoring a broad range of frequencies, determining an optimal frequency range within the broad range of frequencies, determining a dominant brainwave frequency of the subject in the optimal frequency range by identifying which brainwave frequency has the greatest amplitude, exposing the subject to the dominant frequency of the optimal frequency range as the optimal range becomes dominant over less optimal ranges, establishing an individualized feedback program for the subject based on the exposure of the subject to the musical notes, repeating the step of exposing the subject to the musical notes until brain activity is altered to be more optimized for cognitive functioning; and exposing the subject constantly to an ambient sound.

DETAILED DESCRIPTION OF THE PREFERRED EMBODIMENTS

Initially, it should be noted that the method of the present invention requires the use of certain basic hardware and software. In one embodiment, the method utilizes EEG sensors; an EEG amplifier; a computer device; and software loaded on to the computer and configured to operate as disclosed herein.

An artist may want to be able to tap into realms of increased creativity. Corporate managers may want to become more positive and creative leaders. Sales professionals may want to become more attentive and respond more appropriately to the customer's position. Students, particularly those preparing for major examinations, may wish to optimize their cognitive functioning to enhance their capability to study.

Figure 1:
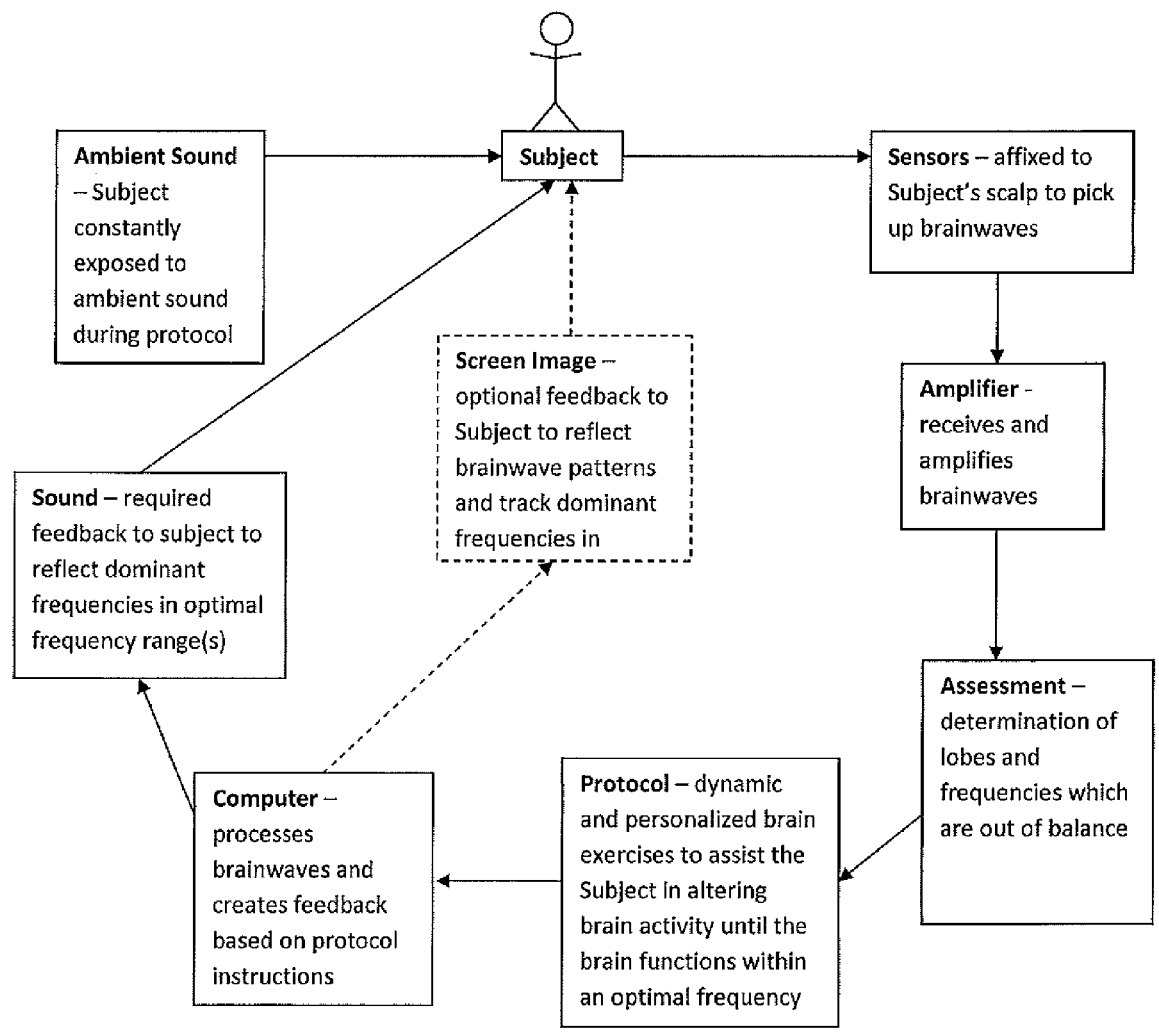
FIG. 1 is a flow chart, illustrating steps in a method for affecting balanced brain functioning with relational ambient sound consistent with an embodiment of the present invention.

Referring now to FIG. 1, in one embodiment, baseline (or current) brainwave activity is first assessed. EEG sensors may be affixed to the subject's scalp to pick up the subject's brainwaves which are then amplified by an EEG amplifier. The location of the sensors on the subject's scalp corresponds to the lobe of the brain (frontal lobe, parietal lobe, occipital lobe, or temporal lobe) that is being monitored. In one embodiment, a broad range of frequencies may be monitored. For example, the broad range of frequencies may be between 0.01 Hz and 49.99 Hz.

In order to monitor the subject's brainwave activity, the subject's dominant brainwave frequency must be determined. The subject's dominant brainwave frequency is simply the brainwave frequency that has the greatest amplitude.

For each lobe and hemisphere of the brain there is an optimal frequency range (between approximately 0.5 Hz and 36 Hz) for each brain state (at rest to fully at task) that lies within the broad range of frequencies. This optimal frequency range will be calculated appropriately for the individual and it may vary depending upon the lobe and the state (relaxed or at task). When the subject's dominant brainwave frequency is within this optimal range as the subject moves from being at rest to being at task, the brain is considered to be more balanced (or homeostatic) and when the subject's dominant brainwave frequency is outside of the optimal range, the brain is considered to be imbalanced.

After it is determined which part(s) of the subject's brain is/are imbalanced, the process of balancing the brain may begin. The computer is programmed to translate at least one frequency within the optimal range into at least one sound. Thus, in each second of time the subject's dominant brainwave frequency within the optimal range is translated into feedback provided to the subject in the form of sound via headphones or speakers.

The sound is a note on a musical scale. In one embodiment, a different musical note may be associated to each frequency within the optimal frequency range. But, it should be clearly understood that substantial benefit may be derived from the same musical note being associated with all frequencies within the optimal frequency range when and only when the optimal frequency range becomes collectively dominant over all other frequency ranges of the with the same frequency extensions (e.g. if the optimal dominant range in a particular lobe is 16-23 Hz when the brain is at task, then any other frequency range containing seven continuous frequencies must be less in total amplitude than the optimal frequency range. Where musical notes are used, a note that is low on the musical scale may be used when the dominant brainwave frequency is at a lower frequency within the optimal frequency range and a note that is high on the musical scale may be used when the dominant brainwave frequency is at a higher frequency within the optimal frequency range.

An individualized feedback program, or protocol, is established for the subject. The purpose of the protocol is to teach the subject's brain how to gravitate on its own toward a balanced state (homeostasis). The protocol is based on the exposure of the subject to the sounds each time the subject's dominant brainwave frequency is within the optimal range. The step of exposing the subject to at least one sound each time the subject's dominant brainwave frequency is within the optimal range is repeated until the brain activity is altered to be more optimized for cognitive functioning and until an amplitude of low frequencies and high frequencies is reducing. The subject's brain learns when it is in a balanced state every time it hears a sound. As the subject's brain continues to "see" itself when it is in a balanced state, it begins to gravitate toward that balanced state.

An analogy to what is being accomplished with the method of the present invention can be found with tuning forks and the principle of resonance. Resonance accounts for the fact that when two tuning forks of the same frequency are placed in close proximity to each other, both will produce a sound even if only one of them is struck. Like a tuning fork, when the brain hears sounds when it generates or inhibits certain frequencies, other parts of the brain respond—resonate—to the frequency of the sound that is heard. Soon, the brain balances itself to the desired frequency, and thereby cuts new neuro-net pathways.

In another embodiment, at least one image (shown to the subject on a screen) may be associated with at least one frequency within the optimal frequency range. The screen image may be a color, a picture, or an object. A different screen image may be associated with each frequency within the optimal frequency range or the same screen image may be associated with all of the frequencies within the optimal frequency range. Similar to the sounds described above, the subject may be exposed to the screen image each time the dominant brainwave frequency is within the optimal frequency range. The step of exposing the subject to the screen image each time the subject's dominant brainwave frequency is within the optimal range may be repeated until the brain activity is altered to be more optimized for cognitive functioning and until an amplitude of low frequencies and high frequencies is reducing. Just as with the use of sound, the subject's brain learns when it is in a balanced state every time it sees the screen image and begins to gravitate toward that balanced state. In a preferred embodiment, the feedback of the screen images may be synchronized with the feedback of the sounds in order to occur simultaneously each time the dominant brainwave frequency is within the optimal frequency range.

While the brain is learning to balance itself, a relationship may be established between the process of balancing and an outside stimulus. The outside stimulus may be an ambient sound, such as but not limited to, the sound of falling rain, blowing wind, crashing waves, etc. The subject may select an ambient sound to his/her liking. The subject is then exposed to the ambient sound during the execution of the protocols. In doing so, the brain begins to relate the process of balancing with the ambient sound. Because this relationship has been established, the subject may later affect the balancing of his/her brain activity by listening to the same ambient sound.

Figure 2:
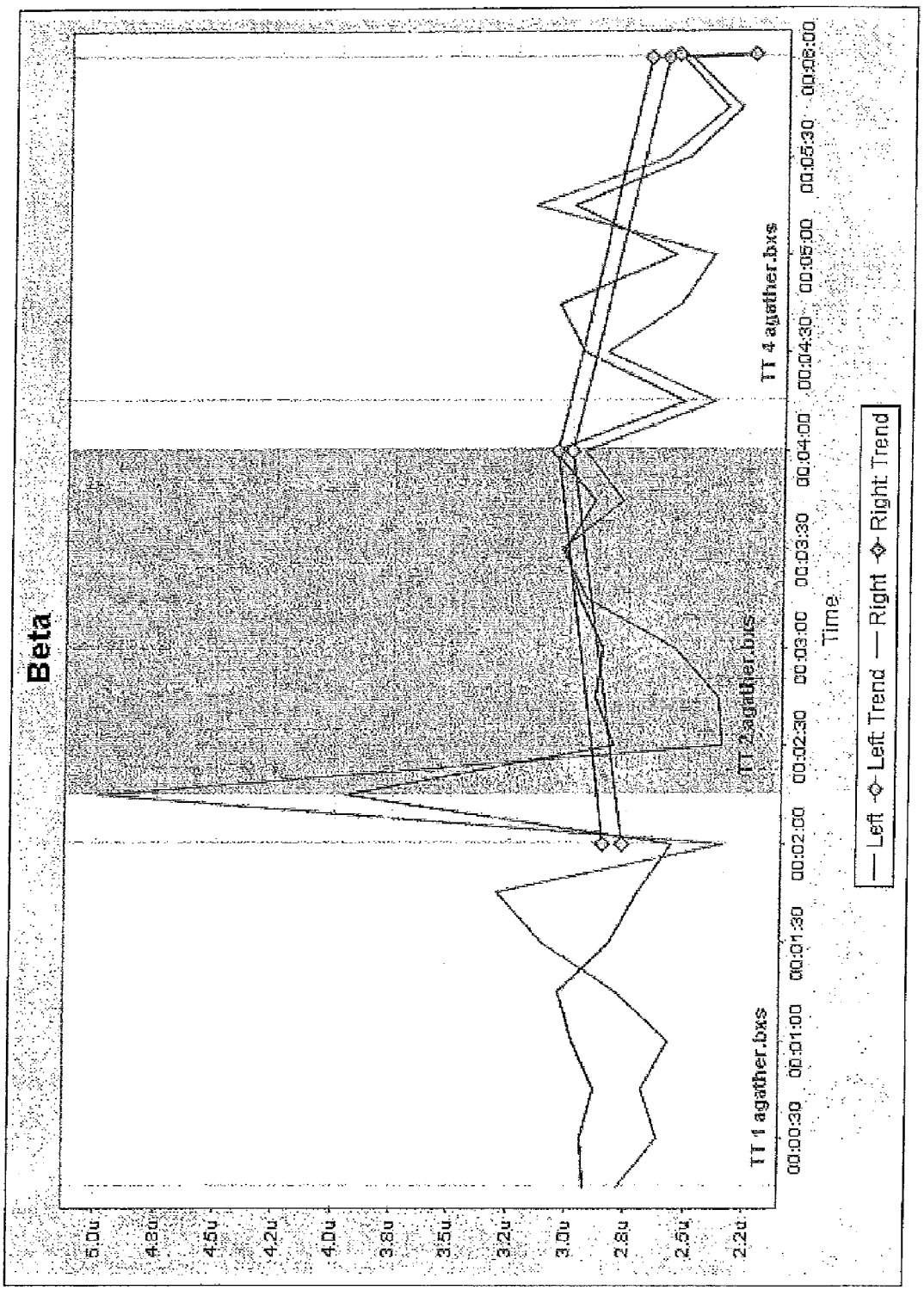
FIG. 2 shows a set of three graphs showing a beta frequency band of a subject's temporal lobes during three different exercises: baseline brain activity, exposing the subject to only ambient sound, and exposing the subject to ambient sound while balancing brain activity.

It is preferred to repeat the brain state conditioning as herein described, so that the desired effects on brain state can be more permanently achieved. Usually, subjects recognize benefits in the first one to three sessions. A brain state conditioning training exercise usually lasts a maximum of 20 minutes and there may be five to seven exercises in a given session. Sessions are usually about 90 minutes in length. Sessions may be completed twice every day. Subjects will usually train ten sessions in one to three weeks, depending on their schedules and personal needs. In FIG. 2 shows three graphs. The graphs show a beta frequency band of a subject's left and right temporal lobes. In the first graph, TT 1, the subject's baseline brain activity is shown. One side of the brain dominates during most of the 2-minute base line period. In the second graph, TT 2, where the subject is exposed only to ambient sounds, the brainwave activity becomes more synchronous. The brain, however, does not relax nor does the synchronous activity of the two lobes continue. In the third graph, TT 4, where the subject has undergone about 20 minutes of brain state conditioning which included a background ambient sound, the brain became much more relaxed and more synchronous.

Statement of Operation

The first step in the brain conditioning method of the present invention is for sensors to be connected to a subject's scalp. It should be clear that although in the preferred embodiment the subject is human, substantial benefit could be derived from an alternative configuration of the present invention in which the subject is non-human, such as another primate. The electromagnetic waves emitted by the subject's brain are amplified and then monitored by a computer.

The subject's baseline brain activity is determined by the computer through a software program. An individualized feedback program (protocol) for the subject is dynamically established by the software based on exposing the subject to a combination of sounds from an external source. Once calculated by the computer program, the subject is exposed to sound automatically generated from the external source and delivered to the subject through headphones or speakers. The software instructs the external source to emit sounds when the subject's dominant brain activity is within an optimal frequency range. The software may also instruct the external source to show a visual image when the subject's dominant brain activity is within an optimal frequency range. In this way, the sounds and the visual images combine to adjust a subject's brain state into a brain state optimized for cognitive functioning.

An ambient sound of the subject's choosing is played for the subject during execution of the protocols. This establishes a relationship between the process of balancing the brain's activity and the ambient sound. Later, because of this relationship, the subject will be able to affect the balancing of his/her brain by listening to the ambient sound.

While the invention has been particularly shown and described with reference to preferred embodiments thereof, it will be understood by those skilled in the art that the foregoing and other changes in form and details may be made therein without departing from the spirit and scope of the invention. For example, the relationship established between the ambient sound and the process of brain state conditioning may also be established between the ambient sound and biofeedback and neurofeedback methods.

I claim:

1. A computer useable medium having program instruction means embodied therein for affecting balanced brain functioning, the computer program instruction means in said computer useable medium comprising the program instruction means for executing the steps of:

determining a baseline brain activity of a subject as reflected in electromagnetic waves emitted by the brain of the subject;

altering brain activity until the brain functions within an optimal frequency range; and establishing a relationship between the step of altering brain activity and an outside stimulus, wherein the step of establishing the relationship between the altering of brain activity and the outside stimulus further comprises:

selecting an ambient sound as the outside stimulus; and exposing the subject to the ambient sound generated from an external source while altering brain activity.

2. The computer useable medium having program instruction means for executing the steps of claim 1 wherein the program instructions further comprise the steps of:

detecting brainwave frequencies in at least one area of the brain with at least two sensors placed on a scalp of the subject; and monitoring the brainwave frequencies to determine the baseline brain activity of the subject.

3. The computer useable medium having program instruction means for executing the steps of claim 2 wherein the at least one area of the brain is one of a frontal lobe, a parietal lobe, an occipital lobe, central strip, a temporal lobe, and a position on a midline of the brain.

4. The computer useable medium having program instruction means for executing the steps of claim 2 wherein the program instructions further comprise the step of monitoring a broad range of frequencies between approximately 0.01 Hz and 49.99 Hz to determine the baseline brain activity.

5. The computer useable medium having program instruction means for executing the steps of claim 4 wherein the program instructions further comprise the step of identifying which brainwave frequency has the greatest amplitude to determine a dominant brainwave frequency within the broad range of frequencies.

6. The computer useable medium having program instruction means for executing the steps of claim 5 wherein the program instructions further comprise the steps of:

determining the optimal frequency range for an area of the brain, wherein the optimal frequency range is within the broad range of frequencies;

associating at least one sound to at least one frequency within the optimal frequency range;

exposing the subject to the at least one sound each time the dominant brainwave frequency is within the optimal frequency range;

establishing an individualized feedback program for the subject based on the exposure of the subject to the at least one sound; and repeating the step of exposing the subject to the at least one sound until the brain activity is altered to be more optimized for cognitive functioning.

7. The computer useable medium having program instruction means for executing the steps of claim 6 wherein the program instructions further comprise the step of repeatedly exposing the subject to the at least one sound until the dominant brainwave frequency falls within the optimal frequency range and an amplitude of low frequencies and high frequencies is reducing.

8. The computer useable medium having program instruction means for executing the steps of claim 6 wherein the at least one sound is at least one musical note generated from an external source.

9. The computer useable medium having program instruction means for executing the steps of claim 8 wherein the program instructions further comprise the step of associating a different musical note to each frequency within the optimal frequency range.

10. The computer useable medium having program instruction means for executing the steps of claim 8 wherein the program instructions further comprise the steps of:
   exposing the subject to a musical note that is low on a musical scale when the dominant brainwave frequency is at a low frequency within the optimal frequency range; and
   exposing the subject to a musical note that is high on the musical scale when the dominant brainwave frequency is at a high frequency within the optimal frequency range.

11. The computer useable medium having program instruction means for executing the steps of claim 6 wherein the program instructions further comprise the steps of:
   associating at least one image to at least one frequency within the optimal frequency range;
   exposing the subject to the at least one image each time the dominant brainwave frequency is within the optimal frequency range; and
   repeating the step of exposing the subject to the at least one image until the brain activity is altered to be more optimized for cognitive functioning.

12. The computer useable medium having program instruction means for executing the steps of claim 11 wherein the image is a color generated from an external source.

13. The computer useable medium having program instruction means for executing the steps of claim 12 wherein the program instructions further comprise the step of associating a different color to each frequency within the optimal frequency range.

14. The computer useable medium having program instruction means for executing the steps of claim 11 wherein the program instructions further comprise the step of synchronizing the step of exposing the subject to the at least one sound with the step of exposing the subject to the at least one image each time the dominant brainwave frequency is within the optimal frequency range.

15. The computer useable medium having program instruction means for executing the steps of claim 1 wherein the program instructions further comprise the step of exposing the subject to the outside stimulus to alter brain activity until the brain functions within an optimal frequency range.

16. A computer useable medium having program instruction means embodied therein for affecting balanced brain functioning with relational sound, the computer program instruction means in said computer useable medium comprising the program instruction means for executing the steps of:
   monitoring a broad range of brainwave frequencies detected from at least two sensors placed on a scalp of a subject;
   determining an optimal frequency range within the broad range of frequencies;
   determining a dominant brainwave frequency of the subject by identifying which brainwave frequency has the greatest amplitude;
   exposing the subject to a musical note each time the dominant brainwave frequency is within the optimal frequency range;
   establishing an individualized feedback program for the subject based on the exposure of the subject to the musical notes;
   repeating the step of exposing the subject to the musical notes until brain activity is altered to be more optimized for cognitive functioning; and
   exposing the subject constantly to an ambient sound.

17. The computer useable medium having program instruction means for executing the steps of claim 16 wherein the program instructions further comprise the step of exposing the subject to a color each time the dominant brainwave frequency is within the optimal frequency range.

18. The computer useable medium having program instruction means for executing the steps of claim 17 wherein the program instructions further comprise the step of synchronizing the step of exposing the subject to the musical note with the step of exposing the subject to the color each time the dominant brainwave frequency is within the optimal frequency range.

19. The computer useable medium having program instruction means for executing the steps of claim 18 wherein the program instructions further comprise the step of repeating the step of exposing the subject to the musical note and the step of exposing the subject to the color each time the dominant brain frequency is within the optimal frequency range until the dominant brainwave frequency consistently falls within the optimal frequency range and an amplitude of low frequencies and high frequencies is reducing.

20. The computer useable medium having program instruction means for executing the steps of claim 16 wherein the program instructions further comprise the step of exposing the subject to the ambient sound to alter brain activity until the brain functions within an optimal frequency range.

21. A computer implemented method for affecting balanced brain functioning comprising the steps of:
   using a computer, receiving baseline brain activity information of a subject as reflected in electromagnetic waves emitted by the brain of the subject;
   using the computer, translating at least one frequency within an optimal range into at least one sound;
   using the computer, providing the at least one sound back to the subject each time a dominant brainwave frequency of the subject is within the optimal range, wherein the brain activity of the subject is altered until the brain functions within an optimal frequency range; and
   providing an outside stimulus to the subject while the brain activity is altered, wherein a relationship is established between the step of altering brain activity and the outside stimulus, and wherein the outside stimulus is ambient sound.

* * * * *